United States Patent [19]
Egel-Mitani et al.

[11] Patent Number: 5,882,883
[45] Date of Patent: Mar. 16, 1999

[54] PROCESS FOR THE PRODUCTION OF SECONDARY METABOLITES

[75] Inventors: Michi Egel-Mitani, Vedbæk; Henrik Møllgaard, Lyngby; Svend Kaasgaard, Søborg; Klaus Nyegaard Kristiansen, Lyngby, all of Denmark

[73] Assignee: Novo Nordisk A/S, Bagsvaerd, Denmark

[21] Appl. No.: 793,786

[22] PCT Filed: Sep. 28, 1995

[86] PCT No.: PCT/DK95/00386

§ 371 Date: Mar. 5, 1997

§ 102(e) Date: Mar. 5, 1997

[87] PCT Pub. No.: WO96/10084

PCT Pub. Date: Apr. 4, 1996

[30] Foreign Application Priority Data

Sep. 28, 1994 [DK] Denmark .................. 1118/94

[51] Int. Cl.$^6$ .............. C12N 1/15; C12N 1/21; C12N 15/63; C12P 37/00
[52] U.S. Cl. ............ 435/43; 435/252.3; 435/254.11; 435/320.1; 435/476; 536/23.2; 536/24.1
[58] Field of Search ................. 435/43, 172.3, 435/252.3, 69.1, 254.11, 254.5, 320.1, 476; 536/23.2, 23.74, 24.1

[56] References Cited

U.S. PATENT DOCUMENTS

| | | | |
|---|---|---|---|
| 4,885,251 | 12/1989 | Ingolia et al. | 435/183 |
| 4,892,819 | 1/1990 | Carr et al. | 435/69.1 |
| 5,108,918 | 4/1992 | Groenen | 435/172.3 |
| 5,474,912 | 12/1995 | Sherman | 435/43 |

FOREIGN PATENT DOCUMENTS

| | | |
|---|---|---|
| 0 200 425 | 12/1986 | European Pat. Off. . |
| 0 260 762 | 3/1988 | European Pat. Off. . |
| 0 354 624 | 2/1990 | European Pat. Off. . |
| 0 357 119 | 3/1990 | European Pat. Off. . |
| 0 379 428 | 7/1990 | European Pat. Off. . |
| 0 448 180 | 9/1991 | European Pat. Off. . |

OTHER PUBLICATIONS

Aharonowitz, Cohen & Martin, "Penicillin And Cephalosporin Biosynthetic Genes: Structure, Organization, Regulation, and Evolution", Annu. Rev. Microbiol. 1992, pp. 461–495.

MacCabe et al., "The Aspergillus Nidulans NPEA Locus Consists Of Three Contiguous Genes Required For Penicillin Biosynthesis", The EMBO Journal vol. 9, No. 1, 1990, pp. 279–287.

Smith et al., "Amplification Of The Isopenicillin N Synthetase Gene In A Strain Of Penicillium Chrysogenum Producing High Levels Of Penicillin", Mol Gen Genet (1989) 216, pp. 492–497.

Pardo et al., "The Upstream Region Of The IPNS Gene Determines Expression During Secondary Metabolism In Aspergillus", Gene 89, 1990, pp. 109–115.

Kück et al., "The 5'–Sequence Of The Isopenicillin N–Synthetase Gene (pcbC) From Cephalosporium Acremonium Directs The Expression Of The Prokaryotic Hygromycin B Phosphotransferase Gene (hph) In Aspergillus Niger", Appl. Microbial Biotechnol, 1989, 31, pp. 358–365.

Veenstra et al., "Strain Improvement Of Penicillium Chrysogenum By Recombinant DNA Techniques", Journal of Biotechnology, 17, 1991, pp. 81–90.

Skatrud et al., "Use Of Recombinant DNA To Improve Production Of Cephalosporin C By Cephalosporium Acremonium", Biotechnology vol. 7, May 1989, pp. 477–485.

Perez–Esteban et al., "Molecular Characterization Of A Fungal Secondary Metabolism Promoter: Transcription Of The Aspergillus Nidulans Isopenicillin N Synthetase Gene Is Modulated By Upstream Negative Elements", Molecular Microbiology, 1993, 9(4), pp. 881–895.

Barredo et al., "Large Amplification Of a 35–Kb DNA Fragment Carrying Two Penicillin Biosynthetic Genes In High Penicillin Producing Strains Of Penicillium Chrysogenum", Curr Genet, 1989, 16, pp. 453–459.

The Merck Index, Eleventh Edition, "Penicillin G Potassium", p. 1123.

The Merck Index, Eleventh Edition, "Pennyroyal", p. 1125.

Arnold L. Demain, "Microbial Secondary Metabolism: A New Theoretical Frontier For Academia, A New Opportunity For Industry", Ciba Found Symp., vol. 171, pp. 3–23. (1992).

*Primary Examiner*—Dian C. Jacobson
*Attorney, Agent, or Firm*—Steve T. Zelson, Esq.; Valeta Gregg, Esq.

[57] ABSTRACT

The invention relates to an improved process for the production of a secondary metabolite comprising (i) fermentation of a microorganism capable of producing said secondary metabolite, and (ii) recovering said metabolite in substantially pure form. Said microorganism has been modified in a manner whereby the expression of one or more of the DNA sequences coding for (a) peptide(s), (a) protein(s) or (an) enzyme(s), involved in or interfering with the biosynthetic pathway of said secondary metabolite, is regulated differently from the regulation of said DNA sequence(s) in the original microorganism. Further contemplated is a process for production of said microorganism, a DNA construct, a vector or transformation vehicle, a microorganism capable of producing secondary metabolite and finally a secondary metabolite product.

25 Claims, 5 Drawing Sheets

PROCESS FOR THE PRODUCTION OF SECONDARY METABOLITES

CROSS-REFERENCE TO RELATED APPLICATIONS

This application is a 35 U.S.C. 371 national application of PCT/DK95/00386 filed 28 Sept. 1995 and claims priority under 35 U.S.C. 119 to Danish application 1118/94 filed 28 Sept. 1994, the contents of which applications are fully incorporated herein by reference.

FIELD OF THE INVENTION

The present invention relates to processes for the production of secondary metabolites in high yields by use of modified microorganisms. The invention further relates to processes for producing the modified microorganisms, DNA constructs and vectors for use in such processes and the modified microorganisms. Lastly the invention relates to secondary metabolites produced by the first mentioned methods.

BACKGROUND OF THE INVENTION

The biochemical pathways of microorganisms can be classified as being part of either primary or secondary metabolism. The pathways of primary metabolism are involved in the catabolism of molecules for energy production or in the synthesis of the building blocks of the cells. Most of these processes are common for all microorganisms. The secondary metabolism is usually anabolic and leads to compounds with no obvious function for the cell.

Among secondary metabolites β-lactam antibiotics are a large family produced in nature by microorganisms. The most important class of β-lactam antibiotics both clinically and economically are the penicillins and the cephalosporins. Their biosynthesis occur via a complex pathway of enzymatic steps.

The unravelling of this pathway has been the subject of many studies during the last few decades. The first two steps in the biosynthetic pathways of the penicillin and the cephalosporin classes of β-lactam antibiotics are identical. Thereafter the biosynthetic pathways to the penicillins and cephalosporins diverge.

The β-lactam biosynthetic pathway

The pathway to the important penicillin species penicillin V is sketched below.

Aminoadipic acid+cysteine+valine→ACV-tripeptide→isopenicillin N→penicillin V

The first step is a condensation of L-α-aminoadipic acid (an intermediate in the lysine biosynthetic pathway in fungi or a degradation product of lysine in bacteria), L-cysteine and L-valine. In cephamycin-producing Actinomycetes, lysine (an amino acid belonging to the so-called aspartate family) is synthesized by the dihydrodipicolinate pathway, which does not include α-aminoadipic acid as an intermediate. In these organisms the precursor is formed by catabolism of lysine by the action of lysine-6-aminotransferase.

In the second step, ACV is oxidatively cyclized by removal of four hydrogen atoms to form the bicyclic penam nucleus (a β-lactam fused to a thiazolidine ring) of isopenicillin N which is present in all penicillins. From here the pathway diverges to penicillins in *Penicillium chrysogenum* and *Aspergillus nidulans* and to cephalosporins and cephamycins in various molds and Actinomycetes. Cephalosporins and cephamycins (7-α-methoxycephalosporins) contain the cephem bicyclic ring system (a β-lactam fused to a dihydrothiazine ring).

The enzymes catalyzing the β-lactam pathway

Formation of the ACV-tripeptide is carried out by the enzyme δ-(L-α-aminoadipyl)-L-cysteinyl-D-valine synthetase (ACVS).

The enzyme catalyzing the second step in the penicillin, cephalosporin and cephamycin biosynthesis is isopencillin N synthase (IPNS or cyclase). IPNS is stimulated by ferrous ions and ascorbate, and requires a reduced environment. As the β-lactam ring is formed during cyclization, isopenicillin N (IPN) is the first compound produced in the pathway with antibiotic activity.

IPNS has been purified from a wide variety of β-lactam producing organisms including *Streptomyces clavuligerus, Streptomyces lactamdurans, Penicillium chrysogenum* and *Cephalosporium acremonium*.

The final step in the penicillin biosynthesis is catalyzed by acyl-CoA:6-aminopenicillanic acid transferase (AT), which has been purified from organisms as e.g. *Penicillium chrysogenum* and *Aspergillus nidulans*.

Most of the enzymes involved in the biosynthesis of β-lactams have been characterized. The genes coding for ACVS, IPNS (cyclase) and AT have been cloned and modified in different ways to increase expression (Martin, J. F., J. Indust. Microorg., 9, p. 73–90, 1992).

The genes encoding the Penicillin biosynthesis

The genes of penicillin biosynthesis in *P. chrysogenum* and *A. nidulans* are named respectively pcbAB, pcbC and penDE and are tightly clustered.

The pcbAB gene, encoding the ACV synthetase (ACVS) in *P. chrysogenum*, is an unusually large gene of about 12 kb without any introns (Smith et al., EMBO J., 9, p. 2743–2750, 1990, Diez et al., J. Biol. Chem., 265, p. 16358–16365, 1990). Transcriptional mapping showed the presence of a long transcript of about 11.5 kb that hybridized with several probes internally in the pcbAB gene. Further two small transcripts of 1.15 kb hybridized with the pcbC or the penDE gene (Martin, J. F., J. Indu. Micr., 9, p. 73–90, 1992).

The transcriptional initiation and termination region of the pcbAB gene has been completely sequenced. The pcbAB gene is linked to the pcbC and penDE genes and is transcribed in the opposite orientation to them.

Also the pcbC gene, encoding isopenicillin N synthase or cyclase of *P. chrysogenum* has been sequenced. The sequence does not contain any introns and the genes of *P. chrysogenum* (Barredo et al., Mol. Gen. Genet, 216, p. 91–98, 1989) are very similar to those of *Streptomyces griseus, N. lactamdurans*, and other Actinomycetes and filamentous fungi.

The penDE gene encodes AT which is the last step of the penicillin biosynthesis (Barredo et al., Gene, 83, p. 291–300, 1989). The penDE gene of *A. nidulans* is very similar to the penDE gene of *P. chrysogenum* and contains three introns in similar positions.

Transcription of the genes of the Penicillin biosynthesis

Several groups have reported transcription analysis of the upstream regions of the pcbC and pcbAB genes. In the fungi, the divergently transcribed genes are separated by about 1 kb. Smith et al. (Bio/Technology, 8, p. 237–240, 1990) used S1 mapping and primer extension to identify transcription initiation sites in the 5' region of the *C. acremonium* pcbC gene. Major and minor pairs of mRNA start sites were found on either side of a pyrimidine-rich block in the promoter region at positions −64 and −72, relative to the first base of the ATG initiation codon. A consensus TATA box was observed 68 bp upstream of the first major transcription start site. A similar motif was found at position −147 in the 5' region of the *A. nidulans* pcbC gene.

The sequence flanking the translation initiation codon matches the consensus fungal sequence. Barredo et al. (Mol. Gen. Genet., 216, p. 91–98, 1989) mapped the start site of *P. chrysogenum* pcbC mRNA by primer extension and showed that a single transcript was made that originated close to the structural gene, starting at position −11.

Similar studies by Kolar et al. (J. Biotechnol., 17, p. 67–80, 1991) with a penicillin production strain of *P. chrysogenum* revealed two major transcription initiation sites, at −131 and −132 as well as at −397.

Primer extension studies of the *A. nidulans* pcbAB gene demonstrated a major mRNA start point at −230 bp. There was found no recognizable core promoter sequences, a situation frequently encountered in fungal genes. As the pcbC and pcbAB genes may be regulated in a coordinate fashion, a search was made for potential regulatory elements, such as receptor sites for transacting proteins, within the intergenic region separating the pcbAB and pcbC genes. A 53-bp region of dyad symmetry is located equidistant from the two genes, but no other extensive sequence identities were detected (McCabe et al., J. Biol. Chem., 266, p. 12646–54, 1991).

Analysis of pcbC mRNA during a *C. acremonium* seven-day fermentation showed a large accumulation of a 1.5-kb transcript between the second and the fourth day. This correlated with the appearance of products of the pathway after isopenicillin N (Smith et al., Bio/Technology, 8, p. 237–40, 1990). The fact that mRNA levels decreased after the fifth day when antibiotics peaked was attributed to stability of the IPNS enzyme.

Regulation of the genes of the penicillin biosynthetic pathway

Little is known about the molecular mechanisms that modify the expression of the genes that regulate the penicillin biosynthesis, despite the fact that many studies show the biosynthetic pathway is subject to numerous metabolic controls.

Recent efforts in this direction have focused on characterizing the DNA regions controlling gene expression and analysing transcription events in terms of critical cell growth parameters that affect antibiotic formation.

ACV synthesis may be the rate-limiting step in biosynthesis of penicillins and cephalosporins and is known to be regulated by glucose in *Penicillium chrysogenum* and *Nocardia lactamdurans*, by phosphate in *Streptomyces clavuligerus* and by ammonium in *Streptomyces clavuligerus* and *Cephalosporium acremonium*. It is also strongly affected by the oxygen transfer rate of the cultures. Regulation of pcbC expression in *C. acremonium* occurs primarily at the transcriptional level. Similar studies of the *S. clavuligerus* pcbC gene show its expression to be under transcriptional control. When cultures of *S. clavuligerus* were grown in rich or defined media, the amounts of pcbC mRNA correlated well with the IPNS enzyme activity and antibiotic production; in defined media, peak values of both occurred much earlier than in rich media (Y. Aharonowitz et al., Annu. Rev. Microbiol., 46, p. 461–95, 1992).

Analysis of mRNA levels of penicillin biosynthetic genes in *A. nidulans*, under conditions where the penicillin synthesis was repressed, showed no transcripts, suggesting common regulation of these genes at the transcriptional level (McCabe et al., EMBO J., 9, p. 279–87, 1990).

Penalva et al. (Genetics and Molecular Biology of industrial Microorganisms, Washington, D.C., Am. Soc. Microbiol., p. 256–61, 1989; Gene, 89, p. 109–15, 1990) showed that in *A. nidulans* the pcbC gene was transcribed only after arrest of cell growth and only then penicillin was detected in the fermentation broth.

A rather different picture was found in *P. chrysogenum*. Levels of pcbC mRNA and IPNS stayed about the same throughout the fermentation, both in a wild-type strain and in a highly mutated overproducer strain (Kuck et al. Appl. Microbiol. Biotechnol., 31, p. 358–65, 1989). The latter exhibited 32- to 64-fold more mRNA than the wild-type strain.

Beatriz Pérez-Esterban et al. (Molecular Microbiology 9:4, p. 881–895, 1993) found that the IPNS promoter of the *A. nidulans* IPNS gene is mostly regulated by upstream negative control elements that act upon a high basal activity. Sequential deletion analysis of three negative cis-acting elements result in a mutated promoter that is 40 times (sucrose broth) or 12 times (lactose broth) more active than the wild type. One of these cis-acting elements is involved in sucrose repression. Strikingly, it is located outside the non-transcribed 525 bp intergenic region and maps to the coding region of the divergently transcribed pcbAB gene. A 5'-deletion up to −56 (relative to the major transcription starting point (tsp)) showed that this region contain information to provide almost half of the maximal promoter activity and allows initiation of the transcription at the correct site. By using total-protein extract from mycelia grown under penicillin producing conditions a DNA-binding activity was detected which specifically binds to a promoter fragment located between −654 and −455 (relative to IPNS tsp). Deletions covering this region partially abolish IPNS promoter activity.

The interpretation of regulatory mechanisms in mutated, high-β-lactam-producing strains is complicated by possible chromosomal aberrations in the cluster of biosynthetic genes. For example, one *P. chrysogenum* overproducer strain had 8–10 copies of the pcbC gene (Smith et al., Mol. Gen. Genet., 216, p. 492–97, 1989) and another contained the pcbC and penDE genes in a DNA segment of at least 35 kb amplified 14-fold (Barredo et al., Curr. Genet., 16, p. 453–59, 1989). The significance of such findings is relevant for attempts to genetically manipulate high producer strains, either through introducing additional copies of β-lactam biosynthetic genes to overcome pathway blocks or by altering regulatory elements.

Amplification of the pcbC-penDE gene cluster of *P. chrysogenum* Wis 54-1255 led to as much as a 40% improvement in production yields (Veenstra et al. J. Biotechnol., 17, p. 81–90, 1991). Increased antibiotic yields were also reported in *A. nidulans* transformants containing multiple copies of pcbAB and pcbC genes (McCabe et al., J. Biotechnol., 17, p. 91–97, 1991).

Attempts to increase cephalosporin C yields in *C. acremonium* and penicillin in *P. chrysogenum* by inserting multiple copies of the pcbC gene were unsuccessful (Skatrud et al. Bio/Technology, 7, p. 477–86, 1989).

A similar result was obtained in terms of penicillin production in a wild-type strain of *A. nidulans* (Penalva et al., Genetics and Molecular Biology of industrial Microorganisms, Washington, D.C., Am. Soc. Microbiol. p. 256–61, 1989).

Relevant patent documents

U.S. Pat. No. 4,885,251 (Eli Lilly) describes a DNA sequence from *C. acremonium* encoding isopenicillin N synthase (IPNS). The IPNS encoding gene sequence was isolated from *C. acremonium*. The intact IPNS gene (pcbC) and associated promoter has been used to construct a vector that drives the expression of IPNS in *C. acremonium*. Further the IPNS promoter has been fused to a hygromycin phosphotransferase-encoding DNA sequence and placed onto *C. acremonium* expression vector.

U.S. Pat. No. 4,892,819 (Eli Lilly) describes a DNA sequence, encoding isopenicillin N synthase (IPNS), comprising the IPNS encoding gene (pcbC) and its promoter from *Penicillium chrysogenum*. The DNA sequence can be placed in an expression vector that function in *P. chrysogenum* and *C. acremonium*. This can be used to increase ultimate expression of a product encoded on a recombinant DNA vector.

EP 200,425 (Eli Lilly) discloses vectors encoding isopenicillin N synthase (IPNS). The vectors permit high level expression of IPNS in *C. acremonium* and *E. coli*. The Cephalosporium vectors are useful for strain improvement, to increase efficiency and yield in fermentations for the production of penicillin and cephalosporin antibiotics. The vectors may also be modified to give vectors for increasing the production yields and efficiency of *P. chrysogenum, Streptomyces clavuligerus* etc. in fermentations.

EP 260,762 (Gist-Brocades) provides a transformation method for preparing Penicillium transformants. The DNA is preferably integrated into a host with stable expression of the structural gene(s) which is introduced. Particularly, complementation of auxotrophy is employed for selection.

EP 354,624 (Gist Brocades) describes a subtraction isolation method for identifying genes associated with the production of secondary metabolites in microorganisms. The method is exemplified with production of penicillin in *P. chrysogenum*.

EP 357,119 (Gist Brocades) discloses the clustered antibiotic biosynthetic genes encoding IPNS, AT and ACVS and are advantageously employed for improvement of production of the antibiotic in microorganisms and for the isolation of other genes involved in the biosynthesis of the antibiotic. The invention is exemplified with improved production of penicillin in *P. chrysogenum*, with the isolation of another clustered biosynthetic gene(s) and with the expression of clustered penicillin biosynthetic genes in *Acremonium chrysogenum*.

EP 448,180 (Gist Brocades) describes a method for modulating production of secondary metabolites which includes modulating the number and/or the size of the organelles, preferably microbodies, in host organism. This is done by altering the expression of a protein present in said organelles; and/or interfering with the cellular control mechanisms for maturation or fission of said organelles; and/or contacting the microorganism with agents capable of regulating the number and/or size of organelles; or modulating the cellular localization of at least one protein, optionally derived from another microorganism, directly or indirectly involved in the production of said secondary metabolites by adding, deleting or altering one or more DNA sequences encoding one or more targeting signals in the gene(s) of one or more of said proteins.

DISCUSSION OF PRIOR ART

Prior art describes how to obtain high accumulated yields of secondary metabolites by increasing the number of copies of the structural gene(s) present in the fermentation microorganism and/or modification of these genes.

However, increasing the number of copies of structural genes present in the fermentation microorganism does not necessarily increase the yield of the secondary metabolites. Apart from incorporation of the extrachromosomal DNA into essential parts of the chromosomal DNA of the microorganism, this can also lead to an expression in a growth phase in which not all the enzymes of the pathway are expressed or where the precursors for the pathway are unavailable. Furthermore, the lack of yield increase can be due to a complex set of interactions between the participants, in the biosynthetic pathways, e.g. precursors and intermediates. This may e.g. be the case when some of the enzymes in the pathway are inhibited by intermediates or products from the pathway. Other examples are accumulation of (unstable) intermediates when bottlenecks arise due to limited enzyme levels or inhibited activity, which in turn may influence the recovery negatively, or when several pathways are competing for the same intermediates.

Furthermore, it is often desirable to produce fermentable products by a continuous fermentation process as the process equipment is used more efficiently. However, this requires that the genes involved in the biosynthesis of the metabolite must all be expressed by growing cells.

When the secondary metabolite is produced using immobilized cells, the cells are usually not growing. It is thus necessary that the genes involved in the biosynthesis of the metabolite are expressed under no-growth conditions.

More specifically, in the fermentation of e.g. penicillin V, if the side-chain precursor is added to the fermentation continuously during the production, the penicillin V slowly starts to accumulate in the broth after a lag phase. The volumetric productivity does not reach a reasonable level until the culture is several hours old. If no side chain precursor is added to the fermentation a mixture of isopenicillin N, 6-aminopenicillanic acid and various "natural" hydrophobic penicillins will accumulate. The presence of these β-lactams represents a waste of substrate and may interfere with the following recovery of the desired penicillin.

SUMMARY OF THE INVENTION

The object of the invention is to overcome some of the above mentioned problems by providing an improved process for the production of a secondary metabolite comprising i) fermentation of a microorganism capable of producing said secondary metabolite, and ii) recovering said metabolite in substantially pure form.

Said microorganism has been modified in a manner whereby the expression of one or several of the DNA sequences coding for (a) peptide(s), (a) protein(s) or (an) enzyme(s), involved in or interfering with the biosynthetic pathway of said secondary metabolite, is regulated differently from the regulation of said DNA sequence(s) in the original microorganism.

Said expression may be initiated at either an earlier or a later fermentation stage in comparison to the original microorganism.

The expression level of said peptide(s), protein(s) or enzyme(s) may be increased at an earlier or later fermentation stage in comparison to fermentation of the original microorganism. The expression may be maintained throughout the fermentation.

According to a preferred embodiment the modification of the microorganism is accomplished by substitution of the promoter(s) region(s) regulating the expression of said DNA sequence(s).

Another object of the invention is to provide a DNA construct comprising a gene encoding the peptide(s), protein (s) or enzyme(s) of interest being connected in a regulatory manner to regulatory element(s)/promoters, which will lead to a regulation that differs from the regulation of the original microorganism.

A specific embodiment of this aspect of the invention relates to a DNA construct comprising the IPNS structural gene (pcbC) and the terminator, which is expressed under control of a penDE gene promoter (ATp).

A still further object of the invention is to provide a vector or transformation vehicle comprising such a DNA construct.

Also the invention relates to a process for the production of a microorganism capable of producing a secondary metabolite, which microorganism has been modified in a manner whereby the expression of one or several of the DNA sequences coding for (a) peptide(s), (a) protein(s) or (an) enzyme(s), involved in or interfering with the biosynthetic pathway of said secondary metabolite, is regulated differently from the regulation of said DNA sequence(s) in the original microorganism.

In a specific embodiment the invention relates to such a microorganism capable of producing clavulanic acid, indole dihydrodiol and antibiotics, especially penicillin.

Finally the invention relates to a secondary metabolite produced by a method according to the first aspect of the invention, especially an antibiotic, clavulanic acid or indole dihydrodiol.

Preferred antibiotics are penicillins, such as penicillin G and penicillin V.

BRIEF DESCRIPTION OF THE DRAWING

The invention will be described in further details in the following parts of the specification with reference to the examples and figures.

DETAILED DESCRIPTION OF THE INVENTION

The invention relates to an improved process for the production of a secondary metabolite comprising i) fermentation of a microorganism capable of producing said secondary metabolite, and ii) recovering said metabolite in substantially pure form.

Said microorganism has been modified in a manner whereby the expression of one or more of the DNA sequences coding for (a) peptide(s), (a) protein(s) or (an) enzyme(s), involved in or interfering with the biosynthetic pathway of said secondary metabolite, is regulated differently from the regulation of said DNA sequence(s) in the original microorganism.

In an embodiment of the process according to the invention said expression is initiated at a different fermentation stage in comparison to the original microorganism. If the expression is initiated at the same time the expression is maintained throughout the fermentation.

The fermentation stage includes, e.g., the lag, growth and stationary phases.

DNA sequences coding for peptide(s), protein(s) or enzyme(s) interfering with the biosynthetic pathway of said secondary metabolite may e.g. be competing (a) peptide(s), protein(s) or enzyme(s) involved with competing pathways.

In another embodiment the expression level of said peptide(s), protein(s) or enzyme(s) is increased at an earlier or later fermentation stage in comparison to fermentation of the original microorganism. The expression may be maintained throughout the fermentation.

An increased expression level of the peptide(s), protein(s) or enzyme(s) in question is defined as an increased activity level.

The alteration of the regulation of the expression of the peptide(s), protein(s) or enzyme(s) may be obtained by genetic modification of one or more of the DNA sequence(s) of said original microorganism. Suitable modifications are e.g. substitution of the promoter and mutations at specific site(s) of the DNA sequence(s) responsible for regulating the initiation and expression of the gene(s). An example of a possible mutation is deletion and addition of one or more bases, using well-known procedures for site-directed or random mutagenesis, e.g. through radiation or chemical treatment.

Further contemplated according to the invention is modification by substitution of the DNA sequence(s) or at least a region in the DNA sequence(s) regulating the initiation and expression of the gene(s).

In a preferred embodiment of the invention said modification is accomplished by substitution of the promoter(s) region(s) regulating the expression of said DNA sequence (s).

The promoter may be any DNA sequence which regulates the expression of said DNA sequences differently from the promoter in the original microorganism.

The above mentioned principles of the process of the invention may be used for the production of any industrially important secondary metabolite where a coordinated expression of one or more peptides, proteins or enzymes is advantageous.

Examples of such relevant secondary metabolites include penicillins, cephalosporins, cephamycins, mono-bactams, chloramphenicol, erythromycin, streptomycin, clavulanic acid, nocardicins, and indole dihydrodiol.

For instance, a coordinated expression of several peptides, proteins or enzymes is advantageous in the production of indole dihydrodiol (for indigo-dyes). Indole dihydrodiol can be produced in *E. coli* after the introduction of a *Pseudononas putida* naphtalene dioxygenase (see Murduoch et al., (1993), Bio/Technology 11, 381).

The precursor for the dioxygenase in indogo synthesis is indole which is an intermediate in the biosynthesis of tryptophane. Indole is usually only present in the cell in low concentrations, but by genetic engineering of the enzyme producing it (i.e. tryptophane synthetase) higher indole levels can be obtained.

In order to stabilize the naphtalene dioxygenase the simultaneous expression of a peptide, ferredoxin, is necessary. By using the same promoters for naphtalene dioxygenase and ferredoxin the stabilization can be obtained.

Further, the use of the same promoter for the modified tryptophane synthetase will lead to a simultaneous production of the substrate, indole.

By limiting the expression of the enzymes to a production phase, the metabolism of the cell will not be loaded with the extra burden required for the production of these peptides, proteins or enzymes in e.g. the growth phase where the buildup of an active cell mass is most important. Another advantage by limiting the time where the genes are expressed is that the likelyhood of genes reverting is limited.

The above points to the general applicability of the principle of the invention to metabolically engineered amino acid overproducing cells where it is important that all genes involved in the biosynthesis are expressed coordinately.

Other examples are the production of phenylalanine (Ikeda, M. and Katsumata, R. (1992) Appl. Envir. Microbiol. 58, 781) or amino acids of the aspartate family (Jetten, M. S. M., and Sinskey, A. J. (1995) Crit. Rev. Biotech. 15, 73).

In the following the production of the antibiotic penicillin will be used as another specific example. It is to be emphasized that penicillin production should only be regarded as an example for illustrating the general principle of the invention.

The penicillin to be produced may for instance be penicillin G or penicillin V.

By controlling the expression of the enzymes in the biosynthetic pathway an earlier onset of the penicillin production can be obtained.

The part of the DNA sequence encoding penicillin to be controlled differently according to the invention may be the region coding for the isopenicillin N synthase (cyclase or IPNS) enzyme.

More specifically said DNA sequence may be modified so that the IPNS promoter is substituted by the promoter regulating the expression of the acyl-CoA:6-amino penicillanic acid transferase enzyme (AT) from P. chrysogenum.

AT is mainly produced early in the fermentation of penicillins while the cyclase peaks when growth decreases. Thus, the combination of the AT-promoter with the cyclase gene will give an earlier expression of this enzyme and an earlier penicillin production.

In a specific example the original microorganism is Penicillium chrysogenum used for producing penicillin. The AT is expressed at a high level in early stage of the fermentation. The IPNS activity increases after a considerable period of fermentation. In order to reduce this lag phase and to induce the penicillin biosynthesis earlier in fermentation, the fermentation strain was transformed with a plasmid comprising the IPNS gene with the AT promoter (ATp IPNS gene).

The exchange of the promoter(s) can result in a coordinated expression of all biosynthetic enzymes for a given metabolite. This leads to a production without accumulation of intermediates in certain phases of the fermentation with the risk of toxic effects or degradation.

A synchronization of the expression of the biosynthetic enzymes can lead to a faster production without or with reduced accumulation of intermediates, which can give purification problems or inhibition of the biosynthesis. It also reduces the degradation of already present β-lactam.

It is advantageous to use the concept of this invention in connection with immobilized cells. Immobilized cells are usually not growing and it is thus necessary to have expression of the biosynthetic genes under no-growth conditions. Some biosynthetic enzymes are primarily produced by growing cells and it is therefore advantageous to introduce a promoter giving increased levels of biosynthetic enzymes in stationary growth phase.

According to the present invention it is possible to select a production phase which is more suitable to the needs of the production. An earlier start of the biosynthesis of the secondary metabolite during the production will lead to a better utilization of the equipment and in some cases to a higher accumulated yield. Alternatively, a delayed production phase may be desirable in order to e.g. build up a certain biomass before the cells starts the biosynthesis of the desired metabolite. This may especially be advantageous if the metabolite is unstable at the conditions used during the cell growth phase or if the metabolite itself or one of its precursors is able to inhibit cell growth. A delayed production phase may then result in a more concentrated production phase, a reduced loss of a labile product, which in turn, leads to the formation of less byproducts, which can be of large significance for the recovery of the metabolite.

Another argument for a period with a concentrated production phase is labile precursors or products. This can either be due to chemical instability or due to the utilization for other metabolic purposes.

An alternative is a constitutive production of a metabolite, i.e. production in all growth phases. In a continuous fermentation it is necessary that all the enzymes are expressed under conditions where at least some growth occur. Therefore regulation factors that allow expression of all biosynthetic enzymes are usually advantageous under these circumstances.

Alternatively a maintenance of expression during growth is necessary in a continuous fermentation process, since it is necessary that all the enzymes are expressed under conditions where growth occurs.

Whether an early or late expression of the biosynthetic enzymes is preferable is very dependent on the specific case. Factors, which may influence the choice, are toxic effects, stability of precursors, intermediates or product, mode of production (e.g. immobilized cells), ease of recovery, and economy.

Another application of the principle is for the regulation of competing metabolic pathways. In some circumstances it will be advantageous to shut down or minimize this competition during the production phase of a metabolite.

This is the case if the competing pathways is draining the primary metabolites which are used for the biosynthesis of the desired product or if the product could itself be metabolized. Further if the primary pathways produce known repressors of the biosynthesis of the desired product.

Another object of the invention is to provide a process for the production of a microorganism capable of producing a secondary metabolite. An original microorganism is modified in a manner whereby the expression of one or more of the DNA sequences coding for (a) peptide(s), (a) protein(s) or (an) enzyme(s), involved in or interfering with the biosynthetic pathway of said secondary metabolite, is regulated differently from the regulation of said DNA sequence in the original microorganism.

In an embodiment of the invention said original microorganism is modified in a manner whereby said expression is initiated at a different fermentation stage in comparison to the original microorganism. If the expression is initiated at the same time the expression is maintained throughout the fermentation.

It is also contemplated to increase the expression level of said peptide(s), protein(s) or enzyme(s) at an earlier or a later fermentation stage in comparison to fermentation of the original microorganism. The expression may be maintained throughout the fermentation.

In a preferred embodiment of the invention said original microorganism is modified by substitution of the promoter (s) region(s) regulating the expression of said DNA sequence(s).

According to the invention said DNA sequence(s), e.g. comprising the promoter(s) or structural gene(s), may be isolated by well-known methods. Thus, the DNA sequence may, for instance, be isolated by establishing a cDNA or genomic library from an organism expected to harbour the sequence, e.g. a cell as described below, and screening for positive clones by conventional procedures. Examples of such procedures are hybridization to oligonucleotide probes in accordance with standard techniques (cf. Sambrook et al., Molecular Cloning: A Laboratory Manual, 2nd. Ed. Cold Spring Harbor Laboratory, Cold Spring Harbor, N.Y., 1989).

A preferred method of isolating a DNA sequence from a cDNA or genomic library is by use of polymerase chain reaction (PCR) using degenerate oligonucleotide probes prepared on the basis of the DNA sequence in question. For instance, the PCR may be carried out using the techniques described in U.S. Pat. No. 4,683,202 or by R. K. Saiki et al., Science 239, p. 487–491, 1988.

Alternatively, the DNA sequence may be prepared synthetically by established standard methods, e.g. the phosphoamidite method described by Beaucage and Caruthers, 1981, or the method described by Matthes et al., 1984. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate), the fragments corresponding to various parts of the entire DNA molecule, in accordance with standard techniques.

Preferably said original microorganism belongs to a genus from the group comprising Penicillium, Cephalosporium, Aspergillus, Nocardia, Streptomyces, Bacillus, Pseudomomas, Cercospora, Micromonospora, other Eubacteria, other Actinomycetes or filamentous fungi, capable of producing industrially important secondary metabolites selected from the group comprising penicillins, cephalosporins, cephamycins, mono-bactams, chloramphenicol, erythromycin, streptomycin, clavulanic acid, nocardicins and indole dihydrodiol.

In a preferred embodiment said original microorganism belongs to a species from the group comprising *Penicillium chrysogenum, Acremonium chrysogenum, Aspergillus nidulans, Nocardia lactamdurans, Streptomyces clavuligerus* and *Pseudomonas putida.*

In another preferred embodiment said original microorganism is a microorganism capable of producing penicillin, especially penicillin G or penicillin V.

In still an embodiment of the invention said DNA sequence comprises the DNA sequence coding for the isopenicillin N synthase (cyclase or IPNS) enzyme.

In a specific embodiment the IPNS promoter is substituted by the promoter (ATp) regulating the expression of the acyl-CoA:6-amino penicillanic acid transferase enzyme (AT).

A further object of the invention is to provide a DNA construct comprising (a) gene(s), which is(are) expressed under the control of a promoter different from the original promoter.

In the DNA construct, a DNA sequence, corresponding to the gene, should be operably connected to a suitable promoter sequence or other expression regulating factors. The promoter may be any DNA sequence which initiates expression of the peptide(s), protein(s) or enzyme(s) at a growth stage different from that of the original microorganism, and may be derived from genes encoding proteins either homologous or heterologous to the host cell.

The DNA construct may also comprise a suitable terminator operably connected to the DNA sequence.

In an embodiment of the invention said DNA construct comprises genes encoding enzymes involved in the secondary metabolism, preferably some of the structural gene(s) encoding proteins for the β-lactam antibiotic biosynthesis, such as the structural gene(s) encoding enzymes for the penicillin biosynthesis.

In a preferred embodiment said DNA construct comprises structural gene(s) encoding the isopenicillin N synthase (cyclase or IPNS) and a promoter of genes involved in β-lactam antibiotic biosynthesis.

In still another preferred embodiment the promoter is a promoter of the genes involved in penicillin biosynthesis, such as the promoter of the acyl-CoA:6-amino penicillanic acid transferase (AT) gene (penDE).

In a specific embodiment of the invention said DNA sequence comprises the IPNS structural gene (pcbC) and the terminator expressed under control of the AT gene (penDE) promoter (ATp).

Alternatively the DNA sequence comprises a promoter of any of the genes e.g. in the primary metabolism.

A further object of the invention is to provide a vector or transformation vehicle comprising a DNA construct. Said DNA construct is preferably one of the above mentioned DNA constructs.

The DNA construct may further comprise a DNA sequence enabling the vector to replicate in the host cell in question. Examples of such sequences are the origins of replication of plasmid pBR322, PUC19, pACYC177, pUB110, pE194, pAMB1, pJC720 and pIJ702.

The DNA construct and/or vector may also comprise a selectable marker, e.g. a gene the product of which complements a defect in the host cell, such as the dal genes from *B. subtilis* or *B. licheniformis*, or one which confers antibiotic resistance such as pleomycin, ampicillin, kanamycin, chloramphenicol or tetracyclin resistance, or positive selective markers, such as hygromycin B, AndS, sC, PyrG, ArgB, TrpC or NiaD.

To direct the enzyme to the desired location within the host cell or into the fermentation media, a targeting signal or a secretory signal sequence (also known as a leader sequence, prepro sequence or pre sequence), respectively, may be provided in the recombinant vector. The targeting signals or secretory signal sequence are joined to the DNA sequence encoding the enzyme in the correct reading frame. Secretory sequences are commonly positioned 5' to the DNA sequence encoding the enzyme, whereas the targeting signal sequences are commonly positioned 3' to the DNA sequence. The targeting signal or secretory signal sequences may be that normally associated with the enzyme or may be from a gene encoding another protein having the desired signal sequence.

Intracellular expression is advantageous according to the present invention.

The procedures used to construct the DNA construct of the invention comprising ligating the DNA sequence(s) encoding the structural gene(s) in question, the promoter, terminator and other elements, respectively, and to insert them into suitable vectors containing the information necessary for replication, are well known to persons skilled in the art (cf., for instance, Sambrook et al., supra, 1989)).

In an specific embodiment the vector or transformation vehicle is pUC19 comprising an operably linked phleomycin resistant expression unit.

Also an object of the invention is to provide a microorganism capable of producing a secondary metabolite. The microorganism has been modified in a manner whereby the expression of one or more of the DNA sequences coding for (a) peptide(s), (a) protein(s) or (an) enzyme(s), involved in or interfering with the biosynthetic pathway of said secondary metabolite, is regulated differently from the regulation of the DNA sequence(s) in the original microorganism.

Preferably the microorganism is produced by the above mentioned process and modified by transformation of a vector or DNA construct of the previous mentioned type.

The microorganism may be transformed with the DNA construct of the invention, conveniently by integrating the DNA construct in the host chromosome, although the DNA construct may also exist as an extrachromosomal entity. However, the integration is generally considered to be an advantage as the DNA sequence is more likely to be stably maintained in the microorganism. Integration of the DNA constructs into the host chromosome may be performed according to conventional methods, e.g. by homologous recombination. Alternatively, the microorganism may be transformed with an expression vector as described below in connection with the different types of host cells.

The microorganism of the invention may be a cell of a higher organism such as a mammal or an insect, but is preferably a microbial cell, e.g. a bacterial or a fungal (including yeast) cell.

Preferably the microorganism belongs to a genus from the group comprising Penicillium, Cephalosporium, Aspergillus, Nocardia, Streptomyces, Escherichia, Bacillus, Pseudomonas, Cercospora, Micromonospora, other Eubacteria, other Actinomycetes or filamentous fungi and is further capable of producing an industrial important secondary metabolite. These are preferably from the group penicillins, cephalosporins, cephamycins, monobactams, chloramphenicol, erythromycin, streptomycin, clavulanic acid, nocardicins and indole dihydrodiol.

The transformation of bacteria, such as *E. coli*, may for instance be effected by protoplast transformation or by using competent cells in a manner known per se.

The filamentous fungus may belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se.

In a preferred embodiment the microorganism belongs to a species from the group comprising *Penicillium chrysogenum, Acremonium chrysogenum, Aspergillus nidulans, Nocardia lactamdurans, Streptomyces clavuligerus, Pseudomonas putida* or *E. coli*.

The medium used to cultivate the microorganisms may be any conventional medium suitable for growing the host cell in question. Suitable media are available from commercial suppliers or may be prepared according to published recipes (e.g. in catalogues of the American Type Culture Collection).

A final object of the invention is to provide a secondary metabolite produced by the above mentioned method.

Preferably the secondary metabolite is an industrially important secondary metabolite selected from the groups of penicillins, cephalosporins, cephamycins, mono-bactams, chloramphenicol, erythromycin, streptomycin, clavulanic acid and nocardicins, especially penicillin, such as penicillin G or penicillin V and pigments, in particular indigo-dyes.

MATERIALS AND METHODS

Strains

B10: *P. chrysogenum* strain (available from Panlabs, 11804 North Creek Parkway South, Bothell Wash. 98011–8805, U.S.A.)

Strain 130: B10 transformed with pME1301 comprising the ATp IPNS gene

Strain 137: B10 transformed with pME1301 comprising the ATp IPNS gene

Clones

Lambda KNK31 clone: Clone containing the penicillin gene cluster, respectively the pcbAB, pcbC and penDE genes.

Vector pUC19: 2.6 kb Asp719-SalI fragment pBR322: 3.9 kb NheI-SalI fragment

Transformation selective marker

*E. coli* Tn5 phleomycin resistant gene expressed by *Aspergillus oryzae* TPI (triose phosphate isomerase) promoter and *Aspergillus niger* AMG (Amyloglucosidase) terminator.

Plasmid pME1243: 2.3 kb EcoRI-SalI fragment penDE promoter—pcbC gene—pcbC terminator in pUC19.

pME1205: Subclone of pcbC and penDE genes from lambda KNK31 in pBR322.

pME1301: 7.6 kb Plasmid containing penDE promoter—pcbC gene—pcbC terminator (2.3 kb), TPI promoter (0.9 kb), Tn5 phleomycin resistant gene (1.1 kb), AMG terminator (0.7 kb) and pUC19 (2.6 kb).

Materials

LCS slant agar: (J. Lein, 1986, "The Panlabs penicillin strain improvement program" in Vanek Z., Hostálek Z. (eds.) Overproduction of microbial metabolites, strain improvement and process control strategies. Butterworth, Boston, p. 105–139).

P-1 seed medium: (J. Lein, 1986)

P-2 fermentation medium: (J. Lein, 1986, lard oil replaced by olive oil))

Tween-80®: (Merck Art. 822187)

LCS medium: Lactose monohydrate 1.5%, corn steep liquor 0.5% peptone 0.5%, NaCl 0.4%, $MgSO_4.7H_2O$ 0.05%, $KH_2PO_4$ 0.06%, $FeCl_3.6H_2O$ 0.0005%, $CuSO_4.5H_2O$ 0.002%, pH 4.8 LCS agar: LCS medium, 2% agar.

Myra cloth (Calbiochem)

Solutions for protoplast formation

BSA: Bovine serum albumin (Sigma A7638)

Solution A: 5 ml contains 1.2M $MgSO_4$, 10 mM $NaH_2PO_4$, pH 5.8, 150 mg Novozym234 (batch #1199), 100 μl chitinase (Sigma, 4 U/ml).

Solution B: 0.6M sorbitol, 100 mM Tris-HCl, pH 7.0

Solution C: 1.2M sorbitol, 10 mM Tris-HCl, pH 7.5, 10 mM $CaCl_2$

Solution D: 60% PEG4000(BDH#29576), 10 mM Tris-HCl, pH 7.5, 10 mM $CaCl_2$.

Methods

DNA was prepared by CsCl density gradient (Maniatis et al., 1982, Molecular cloning, A laboratory manual, Cold Spring Harbor Laboratory, N.Y.).

Cloning of the penicillin gene cluster from *P. chrysogenum*

Genomic DNA from *P. chrysogenum* was isolated according to the procedure of Schwarz-Sommer et al., EMBO J., 3, p. 1021–1028, 1984) and partially digested with Sau3A. Fragments 15–23 kb in size were isolated and ligated to lambda EMBL3 BamHI arms (Promega).

By screening of the genomic library lambda EMBL3 with plaque hybridization method (Maniatis et al., 1982, supra) a clone was found, which hybridised with probes specific for pcbAB, pcbC and penDE, i.e.:

(1) an approx. 400 bp PstI/BamHI fragments containing the pcbAB terminator, (2) an approx. 1 kb NcoI fragment containing the pcbC coding region, and (3) approx. 400 bp Bsu36I/SalI fragment containing the penDE terminator.

Figure 2:
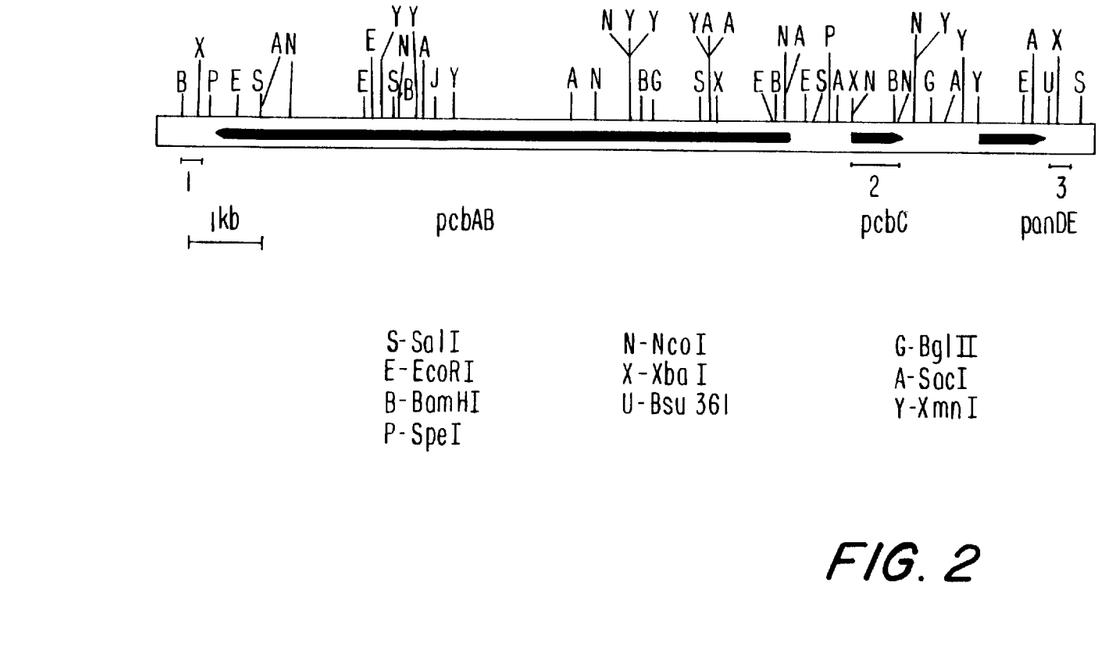
FIG. 2 shows the restriction map of *P. chrysogenum* DNA region comprising the pcbAB, pcbC and penDE genes.

Lambda KNK31 DNA hybridised with all the above mentioned probes (see FIG. 2).

Restriction enzyme sites in lambda KNK31 DNA

Restriction of lambda KNK31 with SalI cuts away the two lambda KNK31 arms (9 and 20 kb, respectively) from the insert, enabling a size estimation of the insert. There are no EcoRI sites in the lambda arms, and the BamHI site used for cloning will statistically be maintained in 25% of the cases when ligated to Sau3A partials. The lambda KNK31 has an 18.6 kb insert and give rise to 6 SalI fragments, 4 EcoRI fragments and 3 BamHI fragments.

Transformation

*Penicillium chrysogenum* production strain B10 was cultured in 2 flasks of 100 ml LCS medium for 36 hrs. at 26° C. Mycelia was collected on Myra cloth and washed thoroughly with 500 ml 0.6M $MgSO_4$, Mycelia was then transferred into a plastic flask and suspended in 5 ml Solution A and placed on ice for 5 min. 750 µl BSA (12 mg/ml) was added to the mycelial suspension and further incubated at 30° C. for 1 to 2 hours with gentle shaking. Protoplast formation was controlled with light microscope.

Protoplasts were collected on Myra-cloth and layered carefully over 5 ml of Solution B. After centrifugation slowly up to 2000 rpm for 15 min., protoplasts, which localized at the interphase between Solution B and Solution A, were taken by pipeting and diluted by adding 2 vol. of Solution C and again centrifuged at 2500 rpm for 5 min. Protoplast pellet was washed twice with Solution C and isolated protoplasts were diluted by adding Solution C to get $1–2 \times 10^7$ cells/ml. 100 µl of protoplasts was used for a transformation.

10 µg DNA prepared by CsCl density gradient was added to the protoplasts and left at room temperature for 20 min. Then 200 µl of Solution D were added and the mixture was left at room temperature for 20 min. 3 vol. of 1.2M sorbitol were then added and protoplast-DNA aggregate was centrifuged at 2500 rpm for 10 min. The pellet was then resuspended by adding 300 µl 1.2M sorbitol and plated on 3 selective plates (100 µl each) containing 50 µg/ml phleomycin and 1.2M Sorbitol in the LCS agar. Plates were incubated at 26° C. until transformants appeared.

Fermentation of *P. chrysogenum*

Lyophilized spores of *P. chrysogenum* (Panlabs B10 strain), were inoculated on 10 ml LCS slant agar after suspension in distilled water containing 0.1% (v/v) Tween-80®. After incubation at 25° C. for 10 days, the spores from the slant surface were suspended in 10 ml of 0.1% Tween-80® and 5 ml were used to inoculate 50 ml P-1 Seed Medium in 300 ml erlenmeyer flasks. The seed culture were incubated at 25° C. on a rotary shaker at 290 rpm. After 48 hours, 2 ml aliquots of seed culture were used for inoculation of the P-2 fermentation medium, 35 ml in 300 ml erlenmeyer flasks. The cultures were incubated at 25° C. at 290 rpm until harvested.

Determination of penicillin V in supernatant from fermentation broth

Firstly, 1 ml of ice cold ethanol was added to 1 ml supernatant, after mixing the proteins were allowed to precipitate for 5 min. on ice bath.

Secondly the samples were centrifuged for 5 min. at 3000 rpm (1550 g), 4° C. The supernatant was diluted with 50 mM Tris/HCl, pH 7.2.

When analysing B10, samples from day 1–2 were normally diluted 200 times and samples from day 3–7 were diluted 2000 times (incl. the 1 fold dilution with ethanol)

The samples were analyzed by HPLC under the following conditions:

Eluent
   100 ml 25 mM Na-phosphate buffer, pH 7.0
   180 ml acetonitrile
   720 ml Milli-Q water
   mixed and degassed by He Flow: 1.5 ml/min Detection: UV 210 nm Column temp. 35° C.

Column: Supelcosil LC-18-DB (25×4.6 mm) with Supel-guard column

Runtime: 12 min.

Retention time (penicillin V): approx. 8.3 min.

Standard: 50 µM Penicillin V (potassium salt)

Preparation of cell extracts from *P. chrysogenum* by sonication

Shake flasks were placed on ice bath until harvest. The cells were harvested as quickly as possible by filtration on Büchnerfunnel coated with one layer Myra cloth (from Calbiochem). Then the cells were washed with at least 2 volumes ice cold 0.9% (W/V) NaCl on the funnel. 2 grams of the cells were weighed into ice cold glass centrifugation tubes, followed by addition of 4 ml 50 mM Tris/HCl, pH 7.2, 5 mM dithiothreitol, 1 mM EDTA and 0.5 mM phenylmethylsulfonyl fluoride (PMSF).

Sonication took place on ice bath for 2 min. (50% duty cycle) followed by centrifugation for 20 min. at 10,000 g. The supernatant was desalted on PD10 column (G25) equilibrated with the same buffer as used for resuspension of the cells, however the PMSF content were reduced to 50 µg/l. For the desalting 2 ml sample was applied on the column followed by 0.5 ml buffer and eluted with another 2.5 ml buffer. The eluate containing the extract was diluted 10 times with 50 mM Tris/HCl, pH 7.2, 5 mM dithiothreitol, 1 mM EDTA, no PMSF. Assay as described in F-9200088 (Available on request from Novo Nordisk A/S).

EXAMPLES

Example 1

The entire penicillin biosynthetic gene cluster including the ACV synthetase gene (pcbAB) was cloned from *P. chrysogenum* B10 in lambda EMBL3.

A phage (lambda KNK31) was found to contain the entire gene cluster.

DNA was isolated (Maniatis et al., supra, 1982) from the lambda KNK31 clone and the insert was mapped by restriction enzyme SalI, EcoRI and BamHI. The restriction enzyme map is displayed in FIG. 2 and below in Table 1.

TABLE 1

| lambda KNK | Insert kb | SalI fragments kb | EcoRI fragments kb | BamHI fragments kb |
|---|---|---|---|---|
| 31 | 18.6 | 1.6, 2.6, 6.0, 2.2, 5.1, 1.1 | 2.5, 7.9, 0.6, 4.3 | 4.7, 2.7, 2.3 |

Example 2
DNA construct

Clone lambda KNK31 was digested with XbaI and BglII isolating a 1427 bp fragment comprising the pcbC gene and the penDE terminator (see FIG. 2).

A 874 bp fragment comprising the penDE promoter was made by PCR (PCR Protocols: A Guide to Methods and Applications, Ed. M. A. Innis, D. H. et al. Academic Press, Inc, 1990)), using lambda KNK31 as a template, and the following primers. The primer tail #1069M contains XbaI site instead of the XmnI site at the original AT promoter.

Primer #1069M SEQ ID NO:1:

XbaII

5'- CTAG TCTAGA GCGGGTCGGAAGATGGGTAAAC - 3'

Primer #1070M SEQ ID NO:2:

SacI

5'- TTCGGCAC GAGCTC TCCTTG - 3'

Figure 1:
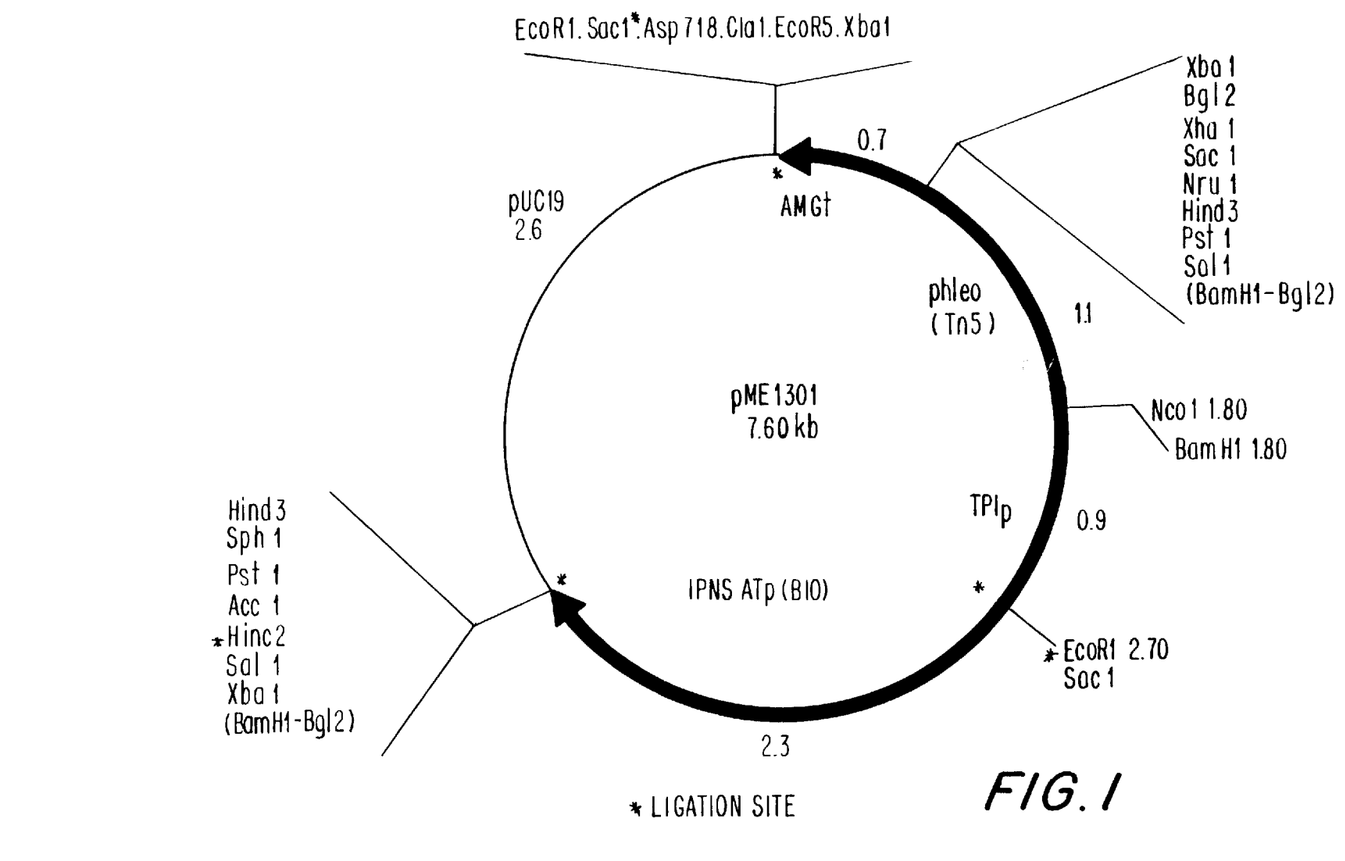
FIG. 1 shows the construction of the pME1301 plasmid, wherein (*) is the ligation site of the three fragment.

The PCR fragment was digested with SacI and XbaI restriction enzymes and the 874 bp fragment was isolated by 0.7% agarose gel electrophoresis. This was ligated to the above mentioned XbaI-BglII fragment of 1427 bp, which contains pcbC structural gene and terminator and 2.6 kb pUC19 vector which was cut with SacI and BamHI enzymes (pME1243). The former fragments was isolated from pME1205 (a subclone of pcbC and penDE genes from lambda clone, KNK31). From pME1243, 2.3 kb EcoRI-SalI fragment, (penDE promoter, pcbC structural gene and pcbC terminator) (ATp IPNS) was taken out and ligated with 2.7 kb Asp718-EcoRI fragment of *E. coli* Tn5 phleomycin resistant gene expression unit (*Aspergillus oryzae* TPI promoter and *Aspergillus niger* AMG terminator) and with pUC19 vector (2.6 Asp718-SalI fragment) This resulted in the pME1301 plasmid (see FIG. 1).

B10 was transformed with pME1301 comprising the ATp IPNS gene. This lead to B10 transformants strain 130 and 137.

Example 3
Biosynthetic enzymes during a fermentation

Figure 3:
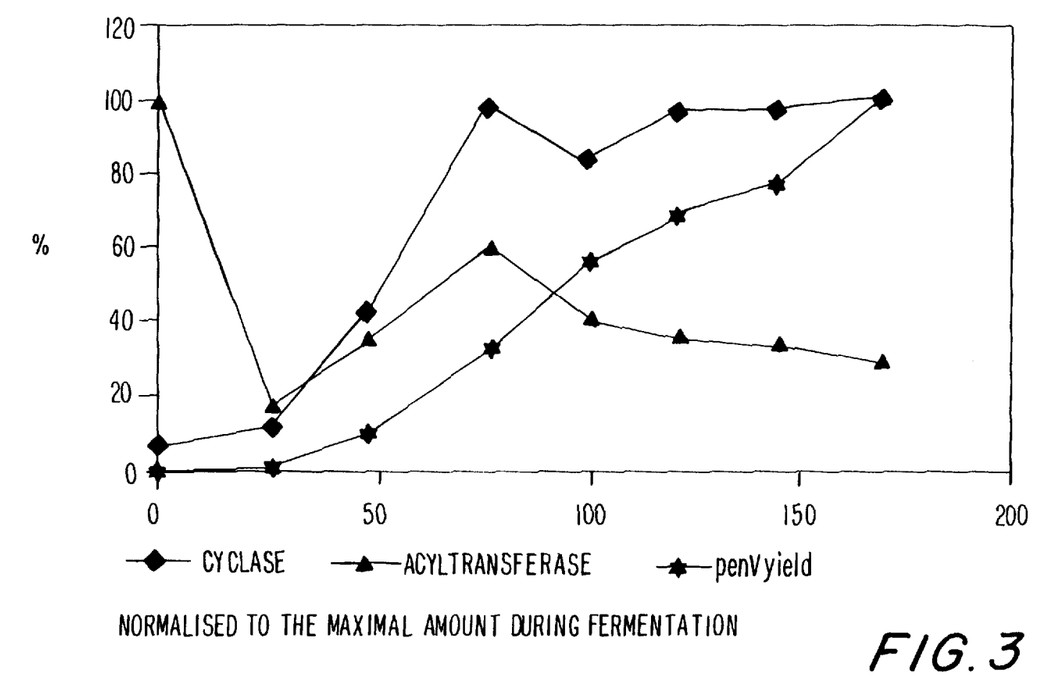
FIG. 3 shows penicillin V yield and the activity levels of two penicillin biosynthetic enzymes, cyclase and acyltransferase, in B10 during a fermentation in shake flasks. The activity is relative to the maximal activity found during the fermentation.

The appearance of cyclase and acyltransferase during a shake flask fermentation of *Penicillium chrysogenum* B10 is shown in FIG. 3. The activities at 0 hours are the activities in the preculture immediately before transfer into the production medium. From the FIG. 3 it is clear that acyltransferase is primarily expressed early in the fermentation while cyclase activity reaches a maximum late in the fermentation. Thus the activities of the two biosynthetic enzymes are uncoordinated. It appears from the figure that the production of penicillin closely follows the curve for cyclase activity.

Example 4
Test of ATp IPNS transformants (130 and 137)

Figure 4:
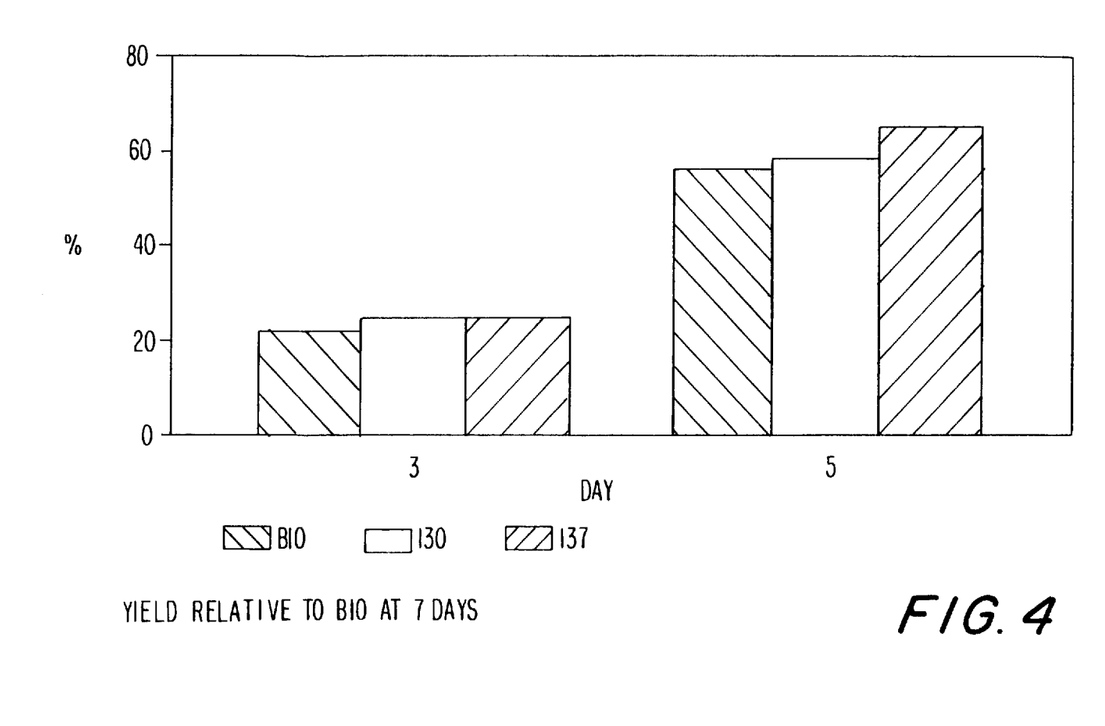
FIG. 4 shows the penicillin yields in shake flasks after 3 and 5 days of fermentation for B10 and two ATp IPNS transformants (130 and 137).

The penicillin production and cyclase activity in the two transformants (130 and 137) produced according to example 2 were tested in shake flasks and compared to the host strain, B10 and the results are given in Table 2, Table 3 and FIG. 4.

It appears that the penicillin production is started earlier in the two transformants compared to B10 and that the accumulated penicillin V production in five days old cultures is increased as well. This corresponds well with the increased cyclase activity both the early and late stages of the fermentation.

In Table 2 the relative cyclase activity and penicillin V yield in 5 day shake flask cultures of ATp IPNS transformants (strain 130 and 137) are displayed. Yields are relative to B10.

TABLE 2

| Strain | n* | Penicillin V yield (% of B10) | IPNS activity (% of B10) |
|---|---|---|---|
| B10 | 61 | 100 ± 10 | 100 |
| 130 | 10 | 115 ± 9 | 196 |
| 137 | 10 | 123 ± 9 | 141 |

*: n is the number of shake flask fermentations of each strain.

By replacing the promoter for cyclase with the promoter from acyltransferase an increased activity of cyclase was obtained in the early part of the fermentation. Furthermore, the elevated level of cyclase activity were maintained throughout the fermentation as is clear from Table 3.

In Table 3 is displayed the relative cyclase activity in 2 and 5 day old shake flask cultures of B10 and two ATp IPNS transformants.

TABLE 3

| Strain | Day 2 | Day 5 |
|---|---|---|
| B10 | 100 (n = 5)* | 100 (n = 61) |
| 130 | 155 (n = 5) | 196 (n = 10) |
| 137 | 148 (n = 5) | 141 (n = 10) |

*: n is the number of shake flasks fermentations of each transformant.

Figure 5:
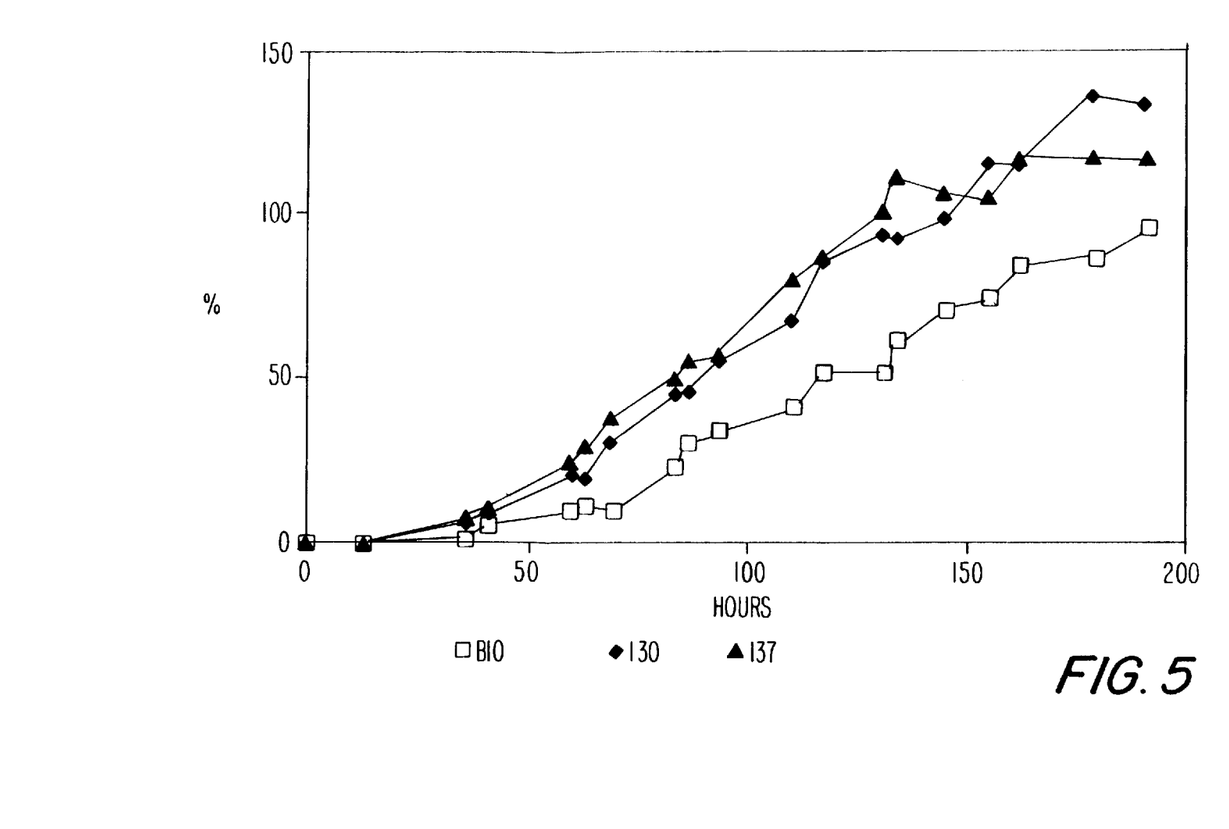
FIG. 5 shows the relative penicillin yield for a 1 liter batch fermentation of B10 and transformants 130 and 137. The curve for B10 is an average of 5 fermentations while the curves for the two transformants each represents the average yields from two fermentations.

The two ATp IPNS transformants (130 and 137) were tested in 1 liter fermenters using the same medium as used in the shake flasks, and the relative accumulated penicillin V yields are given in FIG. 5. From this figure it is evident that by replacing the promoter for cyclase with the promoter for acyltransferase, the penicillin lag phase is reduced and a higher total yield of penicillin was obtained.

It is thus clear that by increasing the expression of cyclase early in the fermentation of penicillin V and maintaining an elevated level of the activity the production of penicillin is started earlier and the accumulated yields are increased.

As will be apparent to those skilled in the art in the light of the foregoing disclosure, many alterations and modifications are possible in practice of this invention without departing from the spirit or scope thereof. Accordingly, the scope of the invention is to be construed in accordance with the substance defined by the following claims.

We claim:

1. A process for the production of a penicillin, comprising:
  (a) constructing a DNA sequence comprising an isopenicillin N synthase (IPNS) gene operably linked to an acyl-CoA:6-amino penicillanic acid transferase (AT) promoter;
  (b) transforming a microorganism capable of producing penicillin with the DNA construct of step (a):
  (c) fermenting said transformed microorganism; and
  (d) recovering penicillin.

2. The process of claim 1, wherein the microorganism is immobilized.

3. The process of claim 2, wherein the fermentation is continuous.

4. The process of claim 1, wherein penicillin is penicillin G or penicillin V.

5. A process for generating a microorganism capable of increased production of a penicillin, comprising transforming a microorganism capable of producing penicillin with a DNA construct comprising an isopenicillin N synthase (IPNS) gene operably linked to an acyl-CoA:6-amino penicillanic acid transferase (AT) promoter.

6. The process of claim 5, wherein the microorganism is immobilized.

7. The process of claim 5, wherein microorganism belongs to a genus from the group comprising Penicillium, Cephalosporium, Aspergillus, Nocardia, Streptomyces, Escherichia, Bacillus, Pseudomonas, Cercospora, Micromonospora, Eubacteria, Actinomycetes, or filamentous fungi.

8. The process of claim 7, wherein the microorganism belongs to a species from the group comprising *Penicillium chrysogenum, Acremonium chrysogenum, Aspergillus nidulans, Nocardia lactamdurans, Streptomyces clavuligerus* and *Pseudomonas putida*.

9. The process of claim 5, wherein the microorganism is capable of producing penicillin G or penicillin V.

10. A microorganism capable of producing penicillin produced by the method of claim 5.

11. A DNA construct comprising a gene encoding isopenicillin N synthase (IPNS) and a acyl-CoA:6-amino penicillanic acid transferase (AT) promoter.

12. The DNA construct of claim 11, further comprising an IPNS structural gene terminator.

13. A vector or transformation vehicle comprising the DNA construct of claim 11.

14. The vector of claim 13, wherein said DNA construct is operably linked to a sequence encoding a targeting signal.

15. The vector of claim 13, wherein said vector further comprises an operably linked phleomycin resistant unit.

16. The vector of claim 13, wherein said vector is pUC19.

17. A process for increasing production of a secondary metabolite by altering the time of expression of a gene encoding an enzyme involved in synthesis of the secondary metabolite, said process comprising the steps of:
  (a) obtaining a microorganism capable of producing said secondary metabolite, wherein said secondary metabolite is penicillin, and wherein said microorganism expresses
    (i) a first gene encoding an enzyme involved in the synthesis of said secondary metabolite, and wherein said first gene is expressed under the control of a first promoter; and
    (ii) a second gene encoding an enzyme involved in the synthesis of said secondary metabolite, and wherein said second gene is expressed under the control of a second promoter, wherein said first and second genes are expressed under control of different promoters; and
  (b) modifying the microorganism of step (a), wherein said modification comprises synchronizing the expression of said second gene with the expression of said first gene, wherein the modified microorganism expresses said first and second genes simultaneously, and wherein production of said secondary metabolite is increased relative to the unmodified microorganism.

18. The process of claim 17, wherein modification comprises placing the first and second genes under regulation of the same promoter.

19. The process of claim 17, wherein the microorganism is immobilized.

20. The process of claim 17, wherein said penicillin is one of penicillin G or penicillin V.

21. The process of claim 20, wherein said second gene encodes isopenicillin N synthase (IPNS) enzyme.

22. The process of claim 21, wherein IPNS promoter is substituted by the promoter (ATp) regulating the expression of the acyl-CoA:6-amino penicillanic acid transferase enzyme (AT).

23. A modified microorganism capable of increasing production of a secondary metabolite by altering the time of expression of a gene encoding an enzyme involved in synthesis of the secondary metabolite generated by the process of claim 17.

24. The microorganism of claim 23, wherein said microorganism belongs to a genus from the group comprising Penicillium, Cephalosporium, Aspergillus, Nocardia, Streptomyces, Escherichia, Bacillus, Pseudomonas, Cercospora, Micromonospora, Eubacteria, Actinomycetes or filamentous fungi.

25. The microorganism of claim 24 selected from the species *Penicillium chrysogenum, Acremonium chrysogenum, Aspergillus nidulans, Nocardia lactamdurans, Streptomyces clavuligerus*, or *Pseudomonas putida*.

* * * * *

UNITED STATES PATENT AND TRADEMARK OFFICE
CERTIFICATE OF CORRECTION

PATENT NO. : 5,882,883
DATED : March 16, 1999
INVENTOR(S) : Egel-Mitani, et. al.

It is certified that error appears in the above-identified patent and that said Letters Patent is hereby corrected as shown below:

Col. 20, line 37, claim 11, delete "a" and insert --an--

Signed and Sealed this

Fourteenth Day of November, 2000

Q. TODD DICKINSON

*Attest:*

*Attesting Officer*          *Director of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

CTAGTCTAGA GCGGGTCGGA AGATGGGTAA AC        3 2

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

TTCGGCACGA GCTCTCCTTG        2 0